US010502669B2

(12) United States Patent
Peterson et al.

(10) Patent No.: US 10,502,669 B2
(45) Date of Patent: Dec. 10, 2019

(54) REAL-TIME VIDEO EXTENSOMETER

(71) Applicant: Illinois Tool Works Inc., Glenview, IL (US)

(72) Inventors: Martin A. Peterson, Wrentham, MA (US); Daniel Dina, North Barrington, IL (US)

(73) Assignee: ILLINOIS TOOL WORKS INC., Glenview, IL (US)

(*) Notice: Subject to any disclaimer, the term of this patent is extended or adjusted under 35 U.S.C. 154(b) by 1 day.

(21) Appl. No.: 15/327,986

(22) PCT Filed: Jun. 25, 2015

(86) PCT No.: PCT/US2015/037723
§ 371 (c)(1),
(2) Date: Jan. 20, 2017

(87) PCT Pub. No.: WO2016/018541
PCT Pub. Date: Feb. 4, 2016

(65) Prior Publication Data
US 2017/0219468 A1 Aug. 3, 2017

Related U.S. Application Data

(60) Provisional application No. 62/029,650, filed on Jul. 28, 2014.

(51) Int. Cl.
*G01B 11/16* (2006.01)
*G01N 3/06* (2006.01)
(Continued)

(52) U.S. Cl.
CPC ............. *G01N 3/068* (2013.01); *G01N 3/08* (2013.01); *G06T 7/246* (2017.01); *H04N 7/10* (2013.01);
(Continued)

(58) Field of Classification Search
CPC .. G01N 3/068; G01N 3/08; G01N 2203/0016;
G01N 2203/0647;
(Continued)

(56) References Cited

U.S. PATENT DOCUMENTS 4,690,001 A * 9/1987 Harvey ................... G01D 5/34
348/294
9,134,885 B2 * 9/2015 Horiuchi ............... G06F 3/0484
(Continued)

FOREIGN PATENT DOCUMENTS

CN          1391680         1/2003
CN        103376065 A      10/2013
(Continued)

OTHER PUBLICATIONS

ISR & WO for PCT/US2015/037723 dated Sep. 16, 2015.
(Continued)

Primary Examiner — Howard D Brown, Jr.
(74) Attorney, Agent, or Firm — McCarter & English, LLP

(57) ABSTRACT

This disclosure relates to a real-time video extensometer. Typically, the apparatus of the disclosure combines the image source, data processing and electrical output on to a single processing board in order to achieve high frequency images and low latency times on data flow. Further, the video processing engine processes the image on a pixel basis and updating the output the intermediate extension/strain result so that after receipt of the final image pixel, a final extension/strain value is achieved and immediately output for evaluation.

10 Claims, 4 Drawing Sheets

(51) Int. Cl.
*G01N 3/08* (2006.01)
*G06T 7/246* (2017.01)
*H04N 7/10* (2006.01)
*H04N 7/18* (2006.01)

(52) U.S. Cl.
CPC ..... *H04N 7/188* (2013.01); *G01N 2203/0647* (2013.01); *G06T 2207/30208* (2013.01)

(58) Field of Classification Search
CPC .......... H04N 7/188; H04N 7/10; G06T 7/246; G06T 2207/30208; G01B 11/16
See application file for complete search history.

(56) References Cited

U.S. PATENT DOCUMENTS

| | | | |
|---|---|---|---|
| 2004/0145724 A1* | 7/2004 | Hayford | G01N 3/02 356/34 |
| 2005/0247136 A1* | 11/2005 | Cross | G01N 3/08 73/826 |
| 2011/0288791 A1* | 11/2011 | Jeppesen | G01N 3/38 702/42 |
| 2014/0142759 A1* | 5/2014 | Schulz | G05B 17/02 700/275 |
| 2014/0153863 A1* | 6/2014 | Sartor | G01M 11/086 385/12 |

FOREIGN PATENT DOCUMENTS

| | | |
|---|---|---|
| CN | 204202569 U | 3/2015 |
| JP | H11264721 A | 9/1999 |
| JP | 3119564 | 3/2006 |

OTHER PUBLICATIONS

PCT Third Party Objection issued in PCT/US2015/037723 on Sep. 2, 2016.
"Image Processing: Open-Source Systems Wins Vision Award", http://www.vision-systems.com/articles/print/volume-14/issue-1/departments/technology-trends/image-processing-open-source-system-wins-version-award.html; Jan. 1, 2009.
"leanXcam.schematic", https://www.scs.ch/fileadmin/images/leanXcam/Schematics.pdf; Nov. 6, 2008.
NEON-1020/1040 Quad Core x86 Smart Camera User's Manual, Jun. 12, 2014.
"The Vision Show 2014: Adlink Technology launches x86 smart camera", http://www.novuslight.com/he-vision-show-2014-adlink-technology-launches-x86-smart-camera_N2490.html; Apr. 10, 2014.
"OpenCV Library Overview", https://web.archive.org/web/20070128064223/http://www.intel.com/technology/computing/opencv/overview.htm, Jan. 28, 2007.
Abhijit Verma, et al. "Strain Measurement Using Image Processing", International Journal of Engineering Research & Technology, Feb. 28, 2013, vol. 2—Issue 2.
Vision Systems Design, "Image Processing: Open-Source system wins Vision Award"; https://www.vision-systems.com/articles/print/volume-14/issue-1/departments/technology-trends/image-processing-open-source-system-wins-vision-award.html; Jan. 1, 2009.
Adlink Technology Inc.; NEON-1020/1040 Quad Core x86 Smart Camera User's Manual; Jun. 13, 2014, pp. 1-16.
Lucero, J. Und Arbel, Y.: Designing High-Performance Video Systems with the Zynq-7000 All Programmable SoC. Application Note: Zynq-7000 All Programmable SoC.XAPP792(v1.0.1), Oct. 16, 2012; www.xilinx.com/support/documentation/application_notes/xapp792-high-performance-video-zynq.pdf.

\* cited by examiner

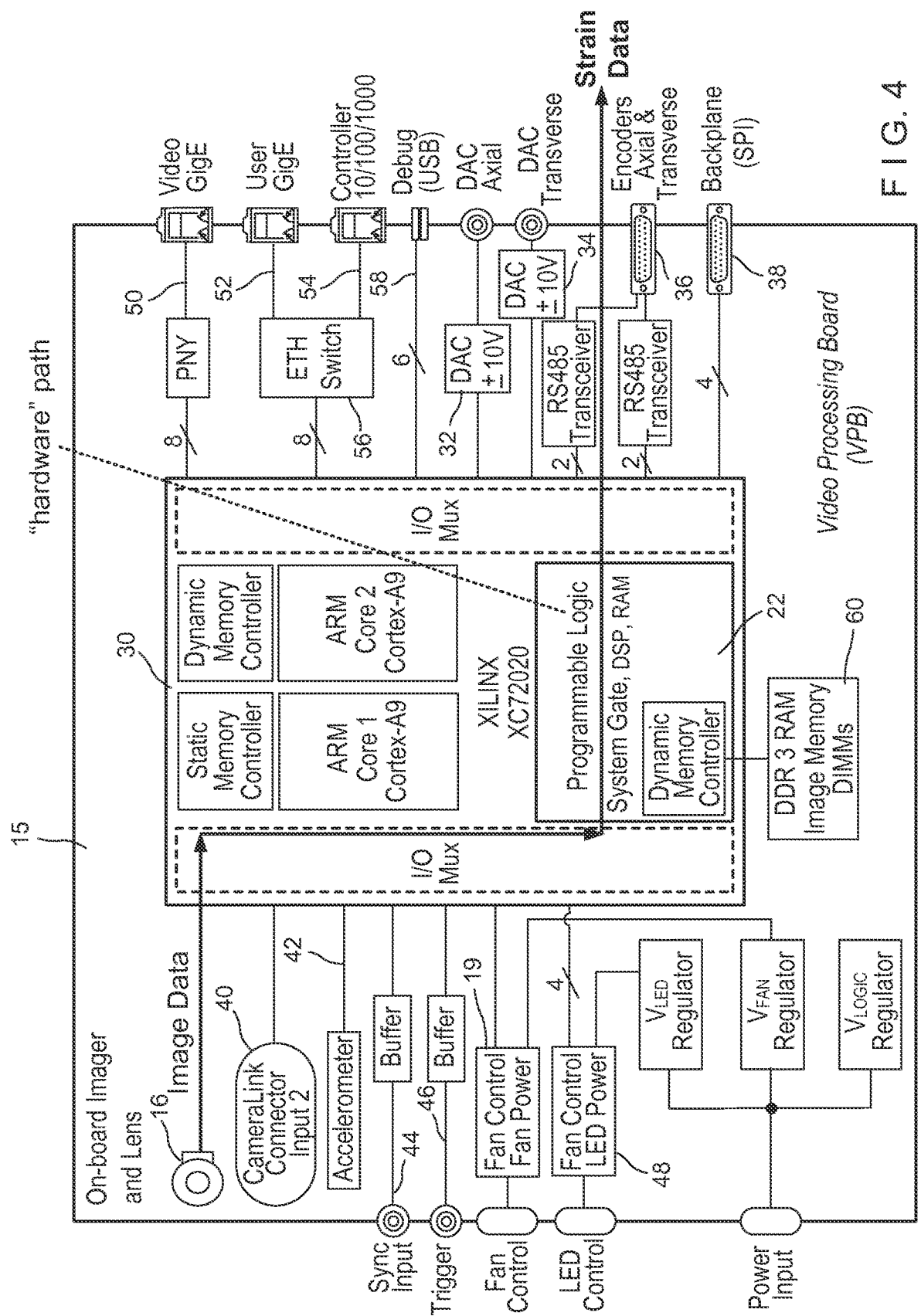
F I G. 4

REAL-TIME VIDEO EXTENSOMETER

RELATED APPLICATIONS

This application is a national phase of International Application No. PCT/US2015/037723 filed Jun. 25, 2015 and claims priority Provisional Application No. 62/029,650, filed on Jul. 28, 2014, the contents of which is hereby incorporated by reference in its entirety and for all purposes.

BACKGROUND OF THE DISCLOSURE

Field of the Disclosure

The disclosure relates to a method of real-time measuring strain and related data by use of video methods.

Description of the Prior Art

Video extensometry is known in the prior art and well-developed for its intended purposes. However, a significant restrictive aspect of measuring strain with a video device is collecting the images at significant speed, providing the images to an image processing engine, processing the images to produce a displacement or strain value, outputting the strain value in a software consumable format and synchronizing it with other data collected via traditional real-time methods (e.g. load cells have electrically balanced bridges).

There are many manufacturers of video processing extensometers. Some of the major companies that provide these are Shimadzo, Zwick and Imetrum. Generally, all of these use the methodology of employing an external machine vision camera, inputting into the PC or video processing hardware and using hardware to convert the data to an electrical signal or having a software interface compatible with the materials testing system.

The prior art includes IPVE and AVE 1 which are manufactured by Instron and which are well developed for their intended purposes. These devices utilize an external camera, PC and analog outputs to capture images and process strain values from these images. The strain data is calculated by software in the PC and output via analog outputs. This is illustrated in FIG. 1.

There are many algorithms for calculating strain from a video images and each has advantages and disadvantages. The main drawback to most of the systems is they use an off-the-shelf high speed machine vision camera, transmit the images via a high speed bus to a processing system, manipulate the images using a standard or dedicated processing system such as a PC or microcontroller and then output the data internally to software on the processing system or via convertors to electrical signals. Typically these systems consume an entire image and work on the array of pixels to produce a strain or displacement value. Computing strain or displacement in this manner is computationally intensive and requires a large microprocessor system. Additionally, to guarantee real-time behavior in order to fulfill many materials testing needs, a real-time operating system is used on the processing system. After computation of the strain or displacement data, it is output to the software on a PC which requires a specialized interface and is not very portable or output via an analog or encoder device. These systems have issues with respect to time latency, integration and required computational power.

OBJECTS AND SUMMARY OF THE DISCLOSURE

It is therefore an object of the present disclosure to develop further improvements with respect to a real-time video extensometer.

Embodiments of this disclosure address the above-identified deficiencies by combining the image source, data processing and electrical output on to a single processing board in order to achieve high frequency images and low latency times on data flow. Further, the data processing engine or FGPA (field programmable gate array) processes the image on a pixel basis and updating the output the intermediate strain result so that after receipt of the final image pixel, a final extension/strain value is achieved and immediately output for evaluation. This hardware and process makes the real-time video extensometer similar to traditional electro-mechanical devices (such as clip-ons) and allows them to be connected and used by materials testing systems in the same manner. The net result of the high speed real-time video processing is the greatly improved accuracy, much faster tracking of the specimen elongation and very low latency data which allows the user to perform and meet a complete range of testing standards.

The real-time video extensometer combines the image inputs, data processing engine and extension/strain data output onto a single video processing board to minimize input and output data latency and maximize processing speed. The video processing board also eliminates the external latency and processing time issues related to operating systems. The primary reason for the improvement with respect to the processing system is the implementation of the entire algorithm on the FPGA (field programmable gate array) portion of the data processing system. The design and implementation makes the entire data path from input occur in hardware and therefore the entire system is deterministic and high speed.

BRIEF DESCRIPTION OF THE DRAWINGS

Further objects and advantages of the disclosure will become apparent from the following description and from the accompanying drawings, wherein:

FIG. 4 is a block diagram of the video processing board of the apparatus of the present disclosure.

DETAILED DESCRIPTION OF THE PREFERRED EMBODIMENT

Figure 1:
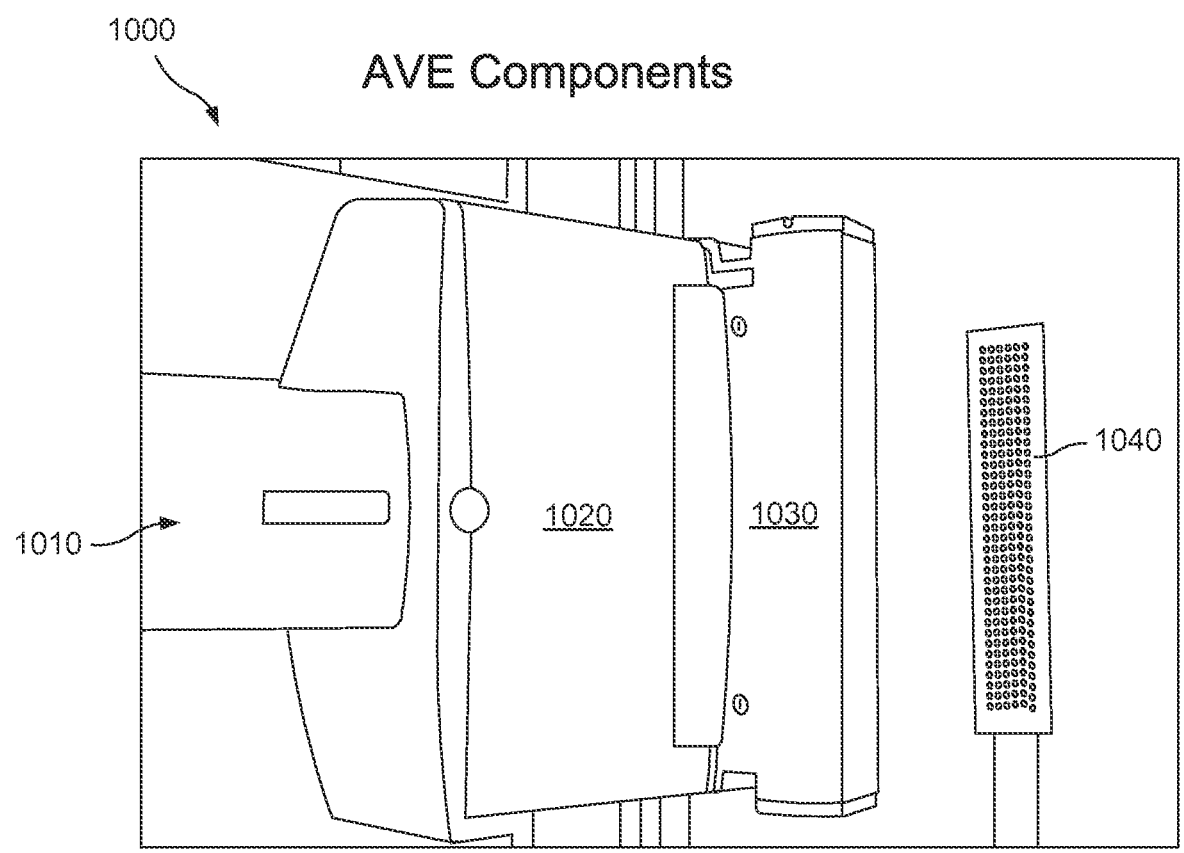
FIG. 1 is a perspective view of the prior art.

Referring now to the drawings in detail wherein like numerals refer to like elements throughout the several views, one sees that FIG. 1 is an extensometer 1000 of the prior art. This extensometer 1000 utilizes an external camera, PC and data communications to capture images and produce extension/strain values. The extension/strain data is calculated by software in both the PC and via analog outputs. More specifically, electronics housing 1010 holds a printed circuit board, a camera (typically with a polarizing and light filter), and lenses for different fields of view. The image received by the camera is taken through a constant density air tube (CDAT) 1020. An integral illumination unit 1030 is fixed to the side of the constant density air tube (CDAT) 1020. Further, a two-dimensional calibration fixture 1040 is provided.

Figure 2:
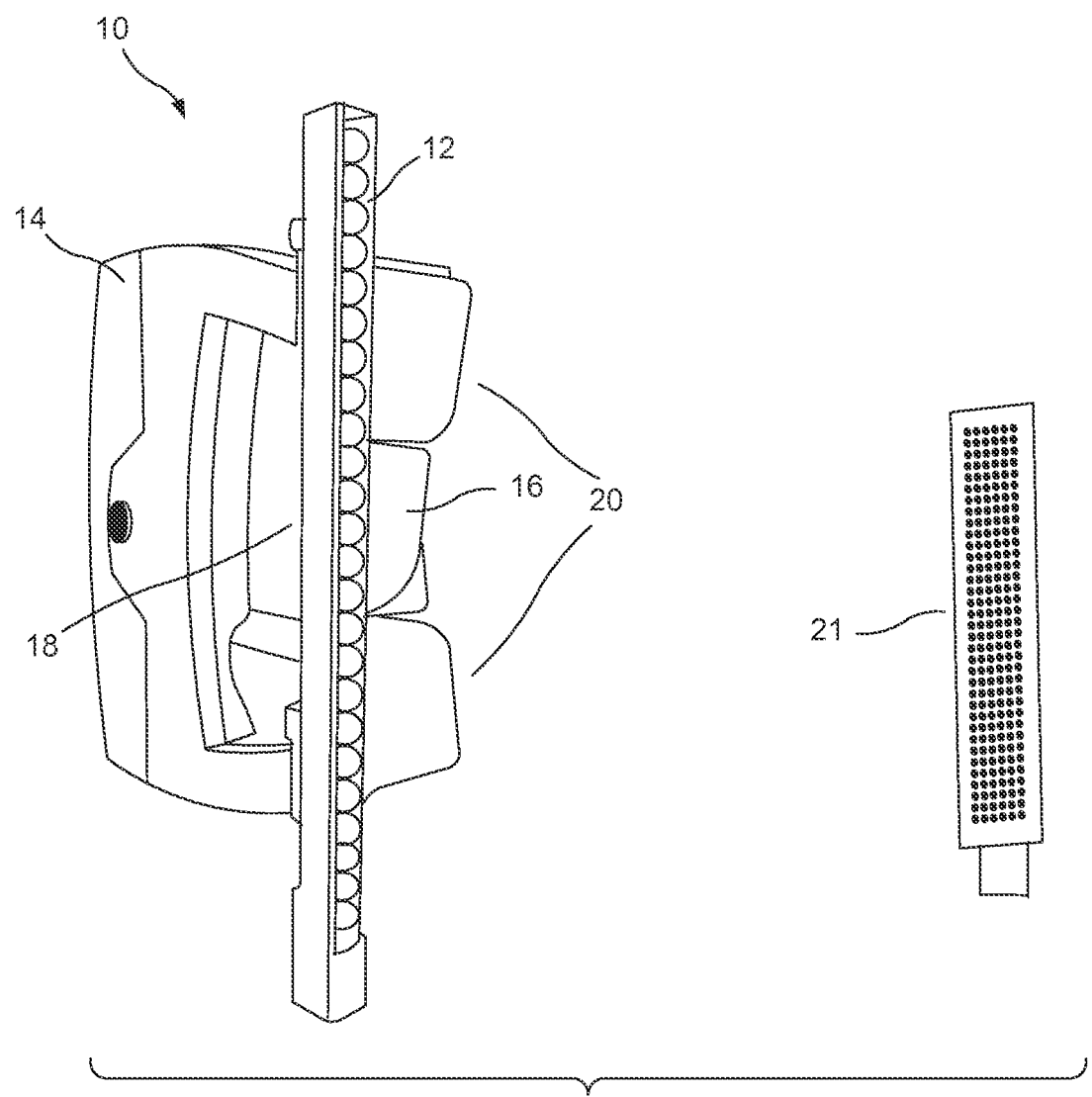
FIG. 2 is a perspective view of components of the apparatus of the present disclosure.

FIG. 2 illustrates the external appearance of an embodiment of the real-time video extensometer 10 of the present disclosure. The real-time video extensometer 10 includes an integral illumination unit 12, implemented as an LED array, to illuminate the specimen (see FIG. 3, element 200, as well as video targets 202 which are painted or otherwise affixed to the specimen 200) under test, as implemented by test frame 190 of FIG. 3. The real-time video extensometer 10 further includes an electronics housing 14, including a printed circuit board or video processing board 15 (also see FIGS. 3 and 4) and a camera or image sensor 16 (also see FIG. 3) with a polarizing filter 17 (see FIG. 3). The camera or image sensor 16 includes various lenses for a range of fields of view. The electronics housing 14 further includes lens access 18 to allow access to the various lenses and a plate to calibrate the real-time video extensometer 10. Additionally, the extensometer 10 includes a constant density air tube (CDAT) 20 and 90 degree light polarization on the integral illumination unit 12 (implemented as an LED array) and the lens of camera 16. A two-dimensional calibration fixture 21, similar to that of the prior art, is additionally used.

Figure 3:
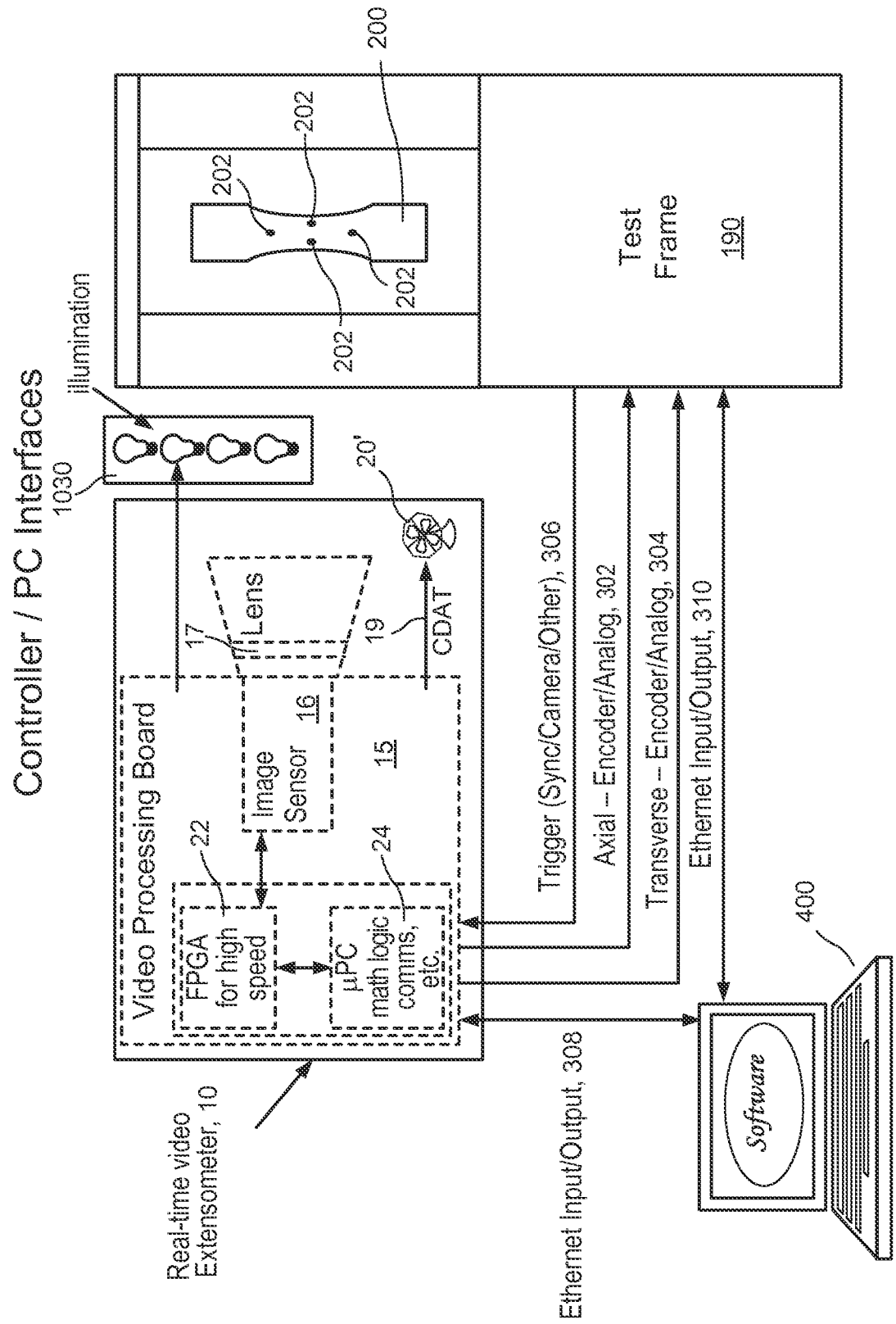
FIG. 3 is a schematic of the apparatus of the present disclosure.

As shown in FIG. 3, the video processing board 15 includes a field programmable gate array (FPGA) 22 (to increase processing speed) and a microprocessor 24. The video processing board further includes line 19 to control the fans 20' of the constant density air tube (CDAT) 20 in order to create a virtual air tube. The real-time video extensometer 10 connects to the materials testing machine (test frame 190) and software utilizing standard interfaces that includes Ethernet, analog, encoder or SPI. This allows the device to be plugged into and used by existing systems without the need for specialized integration software or hardware. The real-time video extensometer 10 provides axial and transverse encoder or analog information to materials testing machine 190 through lines 302, 304, respectively. Materials testing machine 190 provides trigger/synch information to real-time video extensometer 10 through line 306. Real-time video extensometer 10 and materials testing machine 190 exchange real-time test data, including extension/strain data, with the external computer 400 (illustrated as a laptop, although it is envisioned that other computing or processing devices may be implemented) via lines 308, 310, which may be configured via an ethernet connection. Typically, the real-time video extensometer 10 provides extension/strain data to the materials testing machine 190, which in turn, provides stress and extension/strain data to the external computer 400.

FIG. 4 is a block diagram which is an overview of a typical embodiment of the real-time video extensometer 10 of the present disclosure. The video image is input to the system using an onboard image sensor 16 or auxiliary camera link connector input 40 (also shown in FIG. 3). The image data collected is consumed by the processing system entirely in the programmable logic (see FPGA 22 of FIG. 3) of the processing system 30 (such as, but not limited to, a Zync XC7020 SoC) where specialized logic is utilized to calculate multiple axes of extension/strain values (i.e., the change or percentage change in inter-target distance as calculated by video monitoring of the video targets 202 affixed to specimen 200 as shown on FIG. 3) and output the data to materials testing machine 190 (FIG. 3) via the onboard axial or transverse digital-to-analog converter (DAC) 32 or 34, encoder 36 or SPI interface 38 electrical outputs, ultimately leading through lines 302, 304 of FIG. 3. More specifically, Digital-to-Analog Converter (DACs) 32, 34 provide axial and transverse, respectively, strain or displacement signals (typically in the range of negative ten volts to positive ten volts) that allow two separate (typically axial and transverse, or otherwise orthogonal to each other) strain or displacement signals to be output in real-time to the materials testing machine 190. Encoder 36 may include two quadrature encoder outputs that allow two separate strain or displacement signals to be output in real-time to a materials testing controller. The SPI interface 38 communicates digitized signals to any number of PCs, and further outputs in real-time to the materials testing machine 190.

Further functions of the real-time video extensometer 10 are typically implemented by the main printed circuit board implemented as the video processing board 15.

On-board imager and lens (camera) 16 implements a machine vision image sensor to provide high speed images to the processing system 30.

Auxiliary camera link connector input 40 uses standard connectors to allow the use of an off-the-shelf machine vision camera. This can be used in place of the on-board imager and lens (camera) 16 or in conjunction with it. An accelerometer 42 is mounted at the lens 16 to detect acceleration (typically in all three dimensions) for use in the algorithm and/or event detector.

Sync 44 allows an external device such as a materials test machine 190 (see FIG. 3) to provide a synchronization pulse via line 306 (see FIG. 3) to time-stamp images sent to the external computer or PC 400 (see FIG. 3) for later alignment. This time-stamping allows for the addition calculation of a time-dependent stress/strain test result from images (which may be a post-processing result). Similarly, trigger 46 allows an external device such as a materials testing machine 190 to trigger an event via line 306 (see FIG. 3) in the data processing engine and perform functionality such as high speed image buffering and transmission to the external computer or PC 400 (see FIG. 3). This allows for the real-time calculation of a time-dependent stress/strain test result.

Fan control 19 the speed control of the fans 20' of the CDAT 20 to optimize the CDATs 20 for distance. LED control 48 includes two banks of LED/projector array controls to utilize with the two different cameras.

Video GigE block 50 provides an ethernet connection dedicated to high speed image transfers. Similarly, User GigE block 52 and Controller GigE block 54 provide ethernet connections to allow the processing system 30 and the controller f the materials testing machine 190 to communicate via an Ethernet switch 56 to external computer PC 400.

USB port 58 provides debug and messaging to the image processing engine.

DDR 3 RAM 60 provides internal memory to allow storage of images and other data as captured by the high speed image sensor 16. Furthermore, some embodiments may include a SODIMM connection (not pictured) to provide an onboard memory connection to allow the storage of high speed and long duration images from the high speed image sensor 16.

Embodiments of the present disclosure typically have many of the following advantages:

1. High speed data input, data processing and data output.

2. Hardware (FPGA) based algorithm implementation for real-time deterministic behavior without side effects of microprocessor or PC systems.

3. Single board instead of many hardware pieces integrated together.

4. Major cost reduction of the camera, processing system and output device. This provides price flexibility while still achieving very high specifications.

5. Standalone video device directly outputs extension or strain and can be used on many existing systems.

6. Ease of use due to the standalone capability. It is similar to the standard clip-on extensometers.

7. The device can provide data at a rate that can be used for closed loop control.

8. The device can be used on higher speed application due to the increased data rate. For example, this can be used to collect data and perform control on a dynamic system running a sinusoidal waveform.

Substantial advantages of typical embodiments of this disclosure are greatly improved accuracy, much faster tracking of the specimen and very low latency data which allows the user to perform and meet a complete range of testing standards.

A typical testing procedure is illustrated by FIG. 3. The specimen 200 with video targets 202 is engaged within materials testing machine 190. Proximate to the time when specimen 200 is subjected to a stress-inducing load by materials testing machine 190, a command signal is sent to the video processing board 15 and the materials testing machine 190 to the external computer 400. The real-time video extensometer 10 then captures the absolute distance between video targets 202 and monitors the relative movement of video targets 202 to calculate extension/strain in real time. The stress data and the strain data exchanged among the real-time video extensometer 10, the materials testing machine 190 and the external computer 400, and typically organized and displayed via the screen of the external computer 400.

Thus the several aforementioned objects and advantages are most effectively attained. Although preferred embodiments of the invention have been disclosed and described in detail herein, it should be understood that this invention is in no sense limited thereby.

What is claimed is:

1. An extensometer for measuring extension/strain on a testing specimen, comprising:
    an imaging device for generating an image of a testing specimen which is subjected to a stress-inducing load;
    a calculating device, including a microprocessor and a field programmable gate array, for receiving the image of a testing specimen, determining movement of targets on a testing specimen and determining extension/strain from the determined movement of targets, the video device and the calculating device, including the microprocessor and the field programmable gate array, being on a same circuit board; and
    an output device for outputting the determined extension/strain in real-time.

2. The extensometer of claim 1 wherein extension/strain is determined in two orthogonal directions.

3. The extensometer of claim 1 wherein extension/strain is determined in the axial direction and in the transverse direction.

4. The extensometer of claim 1 further including a constant density air tube through which the imaging device views the testing specimen.

5. The extensometer of claim 4 wherein the constant density air tube includes at least one fan, thereby creating a virtual airtube.

6. The extensometer of claim 5 wherein the at least one fan of the constant density air tube is at least partially controlled by the same circuit board as the video device and the calculating device.

7. The extensometer of claim 1 further including an ethernet connection.

8. The extensometer of claim 1 further including an illumination device for illuminating the testing specimen.

9. The extensometer of claim 1 wherein the illumination device emits polarized light.

10. The extensometer of claim 1 further including an auxiliary camera link connector input for receiving an image of a testing specimen which is subjected to a stress-inducing load.

* * * * *